US010489906B2

(12) United States Patent
Holmes et al.

(10) Patent No.: US 10,489,906 B2
(45) Date of Patent: Nov. 26, 2019

(54) PROCESSING OPTICAL COHERENCY TOMOGRAPHY SCANS

(71) Applicant: Michelson Diagnostics Limited, Maidstone, Kent (GB)

(72) Inventors: Jonathan Denis Holmes, West Maling (GB); Richard Whitehead, Lingfield (GB)

(73) Assignee: Michelson Diagnostics Limited, Kent (GB)

( * ) Notice: Subject to any disclaimer, the term of this patent is extended or adjusted under 35 U.S.C. 154(b) by 5 days.

(21) Appl. No.: 15/743,734

(22) PCT Filed: Jul. 13, 2016

(86) PCT No.: PCT/GB2016/052115
§ 371 (c)(1),
(2) Date: Jan. 11, 2018

(87) PCT Pub. No.: WO2017/009641
PCT Pub. Date: Jan. 19, 2017

(65) Prior Publication Data
US 2018/0268542 A1 Sep. 20, 2018

(30) Foreign Application Priority Data
Jul. 15, 2015 (GB) ...................... 1512373

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0066* (2013.01); *A61B 5/02007* (2013.01);
(Continued)

(58) Field of Classification Search
CPC ......... G06T 7/0012; G06T 2207/30104; G06T 2207/30088; G06T 2207/10101; A61B 5/0066; A61B 5/441; A61B 5/02007
(Continued)

(56) References Cited

U.S. PATENT DOCUMENTS

2008/0192236 A1* 8/2008 Smith .................... A61B 1/303
356/73
2009/0247853 A1 10/2009 Debreczeny
(Continued)

FOREIGN PATENT DOCUMENTS

| EP | 2563220 B1 | 7/2014 |
| GB | 2515761 | 1/2015 |
| WO | 2017/009641 | 1/2017 |

OTHER PUBLICATIONS

Trojahn, Carina, et al. "Measuring skin aging using optical coherence tomography in vivo: a validation study." Journal of biomedical optics 20.4 (2015): 045003 (Year: 2015).*
Boone, M. A. L. M., et al. "High-definition optical coherence tomography intrinsic skin ageing assessment in women: a pilot study." Archives of dermatological research 307.8 (2015): 705-720 (Year: 2015).*
(Continued)

*Primary Examiner* — Andrew M Moyer
(74) *Attorney, Agent, or Firm* — Burns & Levinson LLP; Orlando Lopez

(57) ABSTRACT

A method of processing optical coherence tomography (OCT) scans through a subject's skin, the method comprising: receiving at least one OCT scan through the subject's skin, each scan representing an OCT signal in a slice through the subject's skin; processing each OCT scan so as to determine a set of parameters comprising at least a measure of the atrophy of the vascular structure in the epidermis; in which the processing produces a measurement of skin condition dependent upon each of the set of parameters, and the method comprises outputting the measurement of skin condition.

30 Claims, 4 Drawing Sheets

(51) Int. Cl.
    *A61B 5/00*       (2006.01)
    *A61B 5/02*       (2006.01)
(52) U.S. Cl.
    CPC .... *A61B 5/441* (2013.01); *G06T 2207/10101* (2013.01); *G06T 2207/30088* (2013.01); *G06T 2207/30104* (2013.01)
(58) Field of Classification Search
    USPC ........................................................ 382/131
    See application file for complete search history.

(56) References Cited

U.S. PATENT DOCUMENTS

2011/0299754 A1    12/2011   Suri
2016/0262624 A1*   9/2016    Nakajima .............. A61B 5/444

OTHER PUBLICATIONS

Boone et al., "High-definition optical coherence tomography intrinsic skin ageing assessment in women: a pilot study," Arch Dermatol Res (2015) 307: 705-720.
Liew et al., "In vivo assessment of human burn scars through automated quantification of vascularity using optical coherence tomography," Journal of Biomedical Optics, 18(6), Jun. 2013, 10 pages.
Trojahn et al., "Measuring skin aging using optical coherence tomography in vivo: a validation study," Journal of Biomedical Optics, 20(4), Apr. 2015, 8 pages.
GB Search Report, GB Application No. GB1512373.0, dated Dec. 1, 2015, 3 pages.
International Search Report and Written Opinion, International Application No. PCT/GB2016/052115, dated Oct. 20, 2016, 11 pages.

* cited by examiner

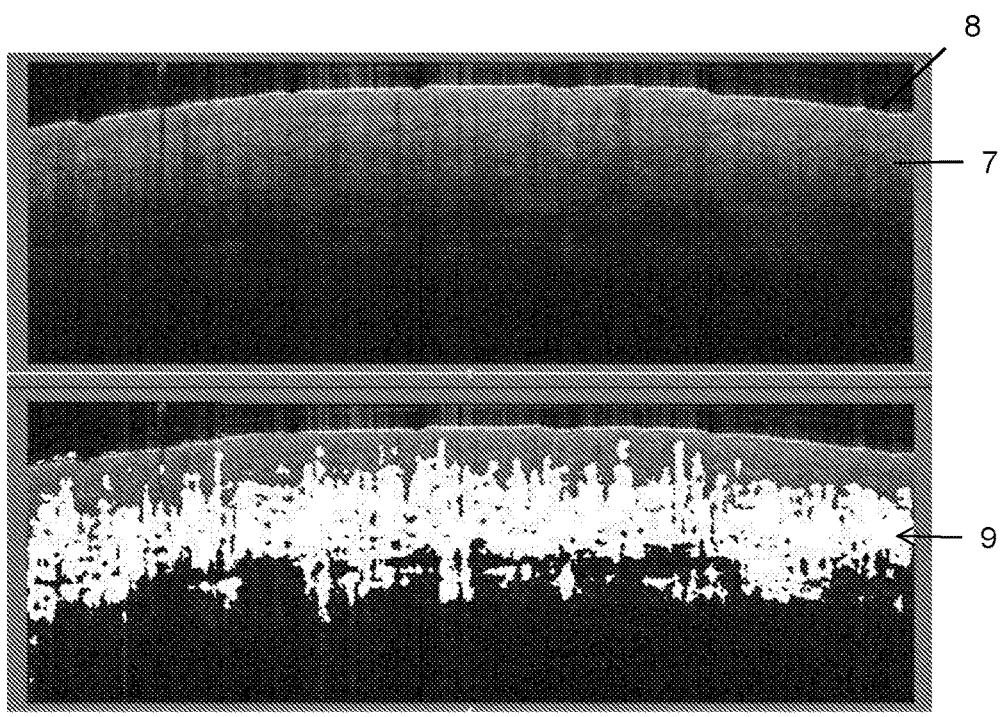

PROCESSING OPTICAL COHERENCY TOMOGRAPHY SCANS

CROSS REFERENCE TO RELATED APPLICATIONS

This application is a U.S. national stage application under 35 U.S.C. § 371 of PCT Application No. PCT/GB2016/052115 filed on Jul. 13, 2016, which is published in English under PCT Article 21(2) as WO 2017/009641 on Jan. 19, 2017, which in turn claims the benefit and priority to the Great Britain Patent Application No. 1512373.0, filed on Jul. 15, 2015. The entire contents of each of which are incorporated herein in their entirety by reference for all purposes.

This invention relates to a method of processing optical coherence tomography (OCT) scans, and associated apparatus.

There is a market need for rapid non-invasive assessment of a subject's skin, for example to aid the developers of cosmetic and skin care products in measuring the effect of their products on subjects, in order to demonstrate and validate their effects to the consumer, and to regulatory authorities in support of their marketing claims.

Various devices have been available for some time that measure certain aspects of the skin. Examples include for example structured light cameras (eg. PRIMOS-lite (www-.canfieldsci.com)) and the confocal microscope (eg. VivaScope product range from Caliber Imaging Diagnostics (www.caliberid.com)). However, these devices suffer from key disadvantages, including:

The measurements take too long to capture and/or to analyse;
The results can be subjective and require a high degree of specialist knowledge to interpret;
The measurements are of the skin surface only and do not capture key aspects of the skin sub-surface, where the impact of pharmaceutical products act (for example the thickness of the epidermis);
The devices do not measure vascular atrophy which is a key measure of skin quality;
The devices only capture a single aspect of the skin, whereas it is desirable to capture in one measurement session, multiple aspects of the skin, including aspects of the skin sub-surface and also aspects of the skin surface;
The devices are cumbersome to use or set up;

Recently, optical scanning techniques such as optical coherence tomography (OCT) have been successfully applied to imaging the sub-surface of the skin in a rapid non-invasive manner for applications in clinical dermatology [Schmitz, 1., et al. (2013) "Optical coherence tomography: its role in daily dermatological practice" German Society of Dermatology.]. OCT has also been applied to applications in cosmetic dermatology [Kauvar et al., (2013) "A pilot study of a novel noninvaive topical under-eye contouring technology", American Academy of Dermatology, Vol 68, (4), Supplement 1, pages AB20]. Most recently, advances in OCT technology have allowed us to detect and measure the vascular network in the upper dermis [as shown in our co-pending United Kingdom patent application, no GB1503196.6], and it is also known that the atrophy of this vascular network is a result of ageing and/or sub-damage of the subject's skin [Ryan T, (2004), "The ageing of the blood supply and the lymphatic drainage of the skin", Micron 35, pp 161-171]. Furthermore, as described in the PCT patent application published as WO2015/001317, it is possible to extract from OCT data, the skin surface topography with a high degree of accuracy and thereby derive and output skin roughness, another parameter of interest to the manufacturers of skin care products. Finally, OCT probes for dermatology use are now available that include miniature cameras that capture video image of the skin that is being measured with OCT. The resulting camera image provides the capability of detecting the colour of the skin and hence an indication of the subject's Fitzpatrick skin type [Fitzpatrick, TB (1975), "Soleil et peau" Sun and skin, Journal de Médecine Esthetique (2), pp 33-34], which is an important factor for the cosmetic dermatologists in assessing the subject's susceptibility to sun damage.

Up until now, no device has been developed that can in one scan procedure capture, process and output key skin quality parameters including, but not limited to, skin roughness and vascular atrophy.

Optical Coherence Tomography (OCT) was invented in 1991 at the Massachusetts Institute of Technology in the United States of America and is commonly used for imaging human tissue of various organs, in particular the eye, and also skin (J. Welzel, "Optical coherence tomography in dermatology: a review," Skin Research and Technology, vol. 7, pp. 1-9, 2001). In particular, we are aware of the VivoSight® OCT device, manufactured and marketed by Michelson Diagnostics Ltd of Orpington, Kent, United Kingdom, which is designed for use by professional dermatologists in the assessment of skin lesions of patients.

The VivoSight OCT device scans the skin and presents to the user images of the skin subsurface structure, in a plane perpendicular to the skin surface (By convention, the OCT device is assumed to be positioned vertically above the skin surface). The resulting two-dimensional image is commonly known in the art as a "B-scan", and comprises many lines of vertical pixels commonly known in the art as "A-lines". Each pixel in the image has a value corresponding to the signal obtained from the OCT device resulting from the skin optical properties at the y-position for that pixel. Also, the VivoSight device can acquire scans at multiple locations across the skin surface in order to build up a series of B-scans across a lesion of interest. This is known in the art as a multi-slice "stack" and can be viewed by the user in a variety of ways to elicit tissue features of medical interest such as nests of cancer cells.

For example, the user can view the stack of B-scans in rapid succession to fly through a lesion area. Also, the stack of data can be re-sampled so that one or more image slices in the horizontal plane (perpendicular to the B-scans) can be extracted and viewed. Horizontal slices are sometimes known in the art as "C-scans". Thus, the C-scan at any desired depth can be viewed. Furthermore, a C-scan and B-scan from a stack can be viewed simultaneously. All of this is well known to those skilled in the art of OCT and more generally medical imaging.

We are aware of the European Patent published as EP 2 563 220 B1, which discloses the use of OCT scanning in determining the "plumpness" of skin by determining the rugosity and length of rete ridges combined with the thickness of the dermis relative to the epidermis.

According to a first aspect of the invention, there is provided a method of processing optical coherence tomography (OCT) scans through a subject's skin, the method comprising:
receiving at least one OCT scan through the subject's skin, each scan representing an OCT signal in a slice through the subject's skin;

processing each OCT scan so as to determine a set of parameters comprising at least a measure of the atrophy of the vascular structure in the epidermis;

in which the processing produces a measurement of skin condition dependent upon each of the set of parameters, and the method comprises outputting the measurement of skin condition.

Thus, a measurement can be provided, which has been found to be indicative of skin health and aging; in particular it can provide a meaningful indication of skin health that is of value to a skin products manufacturer. It can be used to, for example:

provide a cosmetic measurement of the user's skin and/or its condition;

provide an indication of the aging of the user's skin; or provide an indication of the actual or apparent age of the skin with reference to the subject's actual age;

measure the change in skin condition, and typically in particular changes in vascular atrophy and/or changes in skin roughness, brought about by the action of a skin product, such as a skin care product.

The determination of the measure of skin atrophy may comprise determining the position of blood vessels in the user's skin. This determination may further comprise determining a distribution of a numerical density (that is, the number in a given volume) of blood vessels with depth through the user's skin, and typically determining a threshold depth in the distribution moving through the user's skin from the skin's surface through the skin at which the numerical density of blood vessels in the user's skin exceeds or reaches a threshold. The determination of the measure of atrophy, and the measure of atrophy itself, may therefore comprise a determination of the volume density (that is the volume occupied in a given volume) of blood vessels at the threshold depth. This is a useful indication of the condition and particularly the aging of a user's skin, which can conveniently be assessed from OCT scans.

The measure of atrophy may be determined based upon the volume density. In particular, the measure of atrophy may be determined using a lookup table which maps the volume density together with at least one of the location of the user's skin on the user's body, the threshold depth, the age and gender of the user to a value forming the measure of atrophy.

The set of parameters may further comprise the skin reflectivity. As such, the determination of the skin reflectivity may comprise finding the average intensity of the OCT signal in each scan at the top surface of the user's skin. Alternatively, the determination of the skin reflectivity may be obtained by calculating a weighted average of the intensity of pixels in the OCT scan within a predetermined depth of the top surface of the skin, with greater weight being assigned to the top surface and less weight (typically linearly) to pixels with greater depth.

The set of parameters may further comprise the skin structure as a function of the depth through the skin. The skin structure may comprise a determination of the position the skin surface in each scan, which may set a reference datum for depth. The determination of skin structure may also comprise the identification of layers within the user's skin, and the comparison of the intensity of the scans within each layer to an expected intensity for each layer. Typically, the method would comprise determining the mean and/or standard deviation intensity within at least one sample area in each layer, and comparing the mean and/or standard deviation intensity within each layer to an expected mean and/or standard deviation intensity for each layer. The method may alternatively comprise determining the mean attenuation coefficient within the layer, which is the rate at which the intensity falls with increasing depth within the layer.

The set of parameters may further comprise the skin roughness. The determination of the skin roughness may comprise the determination of the mean deviation of the skin position from the mean skin position (known as $R_a$), the range of skin position from the highest peak to lowest valley (known as $R_z$) or the root mean square deviation of the skin position (known as $R_q$).

The method may further comprise determining a set of additional parameters otherwise than from the OCT scans, and using each of the set of additional parameters in the determination of the measurement of skin condition.

For example, the set of additional parameters may comprise the skin tone of the subject. The determination of the skin tone of the subject may comprise imaging of the region of skin scanned with OCT with a camera attached to the OCT probe. Typically, the camera would be equipped with a light source, which may have a known spectrum in the visible wavebands, such as a white LED, and analysing the resulting colour of the camera image of the skin, typically from the mean colour channel (for example, red, green or blue) signal strengths by comparison with limits in a look-up table or otherwise. The determination of skin tone may approximately classify the skin type of the subject according to subtypes, for example, pale white, white, cream, moderate brown, dark brown, deep brown.

The determination of the measurement of skin condition may comprise the comparison of each of the parameters with a predetermined value for that parameter and assigning a measurement of skin condition based upon a divergence between the parameter and the predetermined value. The predetermined value may be age and/or gender dependent. The measurement of skin condition may comprise an age difference between a predetermined skin condition—typically an ideal skin condition—for a user of given age and/or gender and/or skin type and the condition of the skin as determined based on each parameter. The determination of the measurement of skin condition may comprise the determination of a partial age difference based on each parameter, and then combining each of the partial age differences, typically by summing. The partial age differences may be determined by using a lookup table for each parameter, each lookup table mapping the parameter to a partial age difference.

According to a second aspect of the invention, there is provided an optical coherence tomography (OCT) image processing apparatus, comprising a processor, a display coupled to the processor and storage coupled to the processor, the storage carrying program instructions which, when executed on the processor, cause it to carry out the method of the first aspect of the invention.

The image processing apparatus may comprise an OCT apparatus by means of which the OCT scans are captured. As such, the image processing apparatus may comprise an OCT probe arranged to generated interferograms, and the processor may be arranged to generate the images from the interferograms. As such, the image processor may be arranged to process the images as they are captured.

Alternatively, the image processing apparatus may be separate from any OCT apparatus and may be arranged to process the images subsequent to their capture. As such the image processing apparatus may comprise data reception means (such as a network connection or media drive) arranged to receive the images for processing.

There now follows, by way of example only, description of embodiments of the invention, described with reference to the accompanying drawings, in which:

FIG. 2 shows an OCT scan of healthy tissue;

FIG. 3 shows the areas of movement in the OCT scan of FIG. 2;

Figure 1:
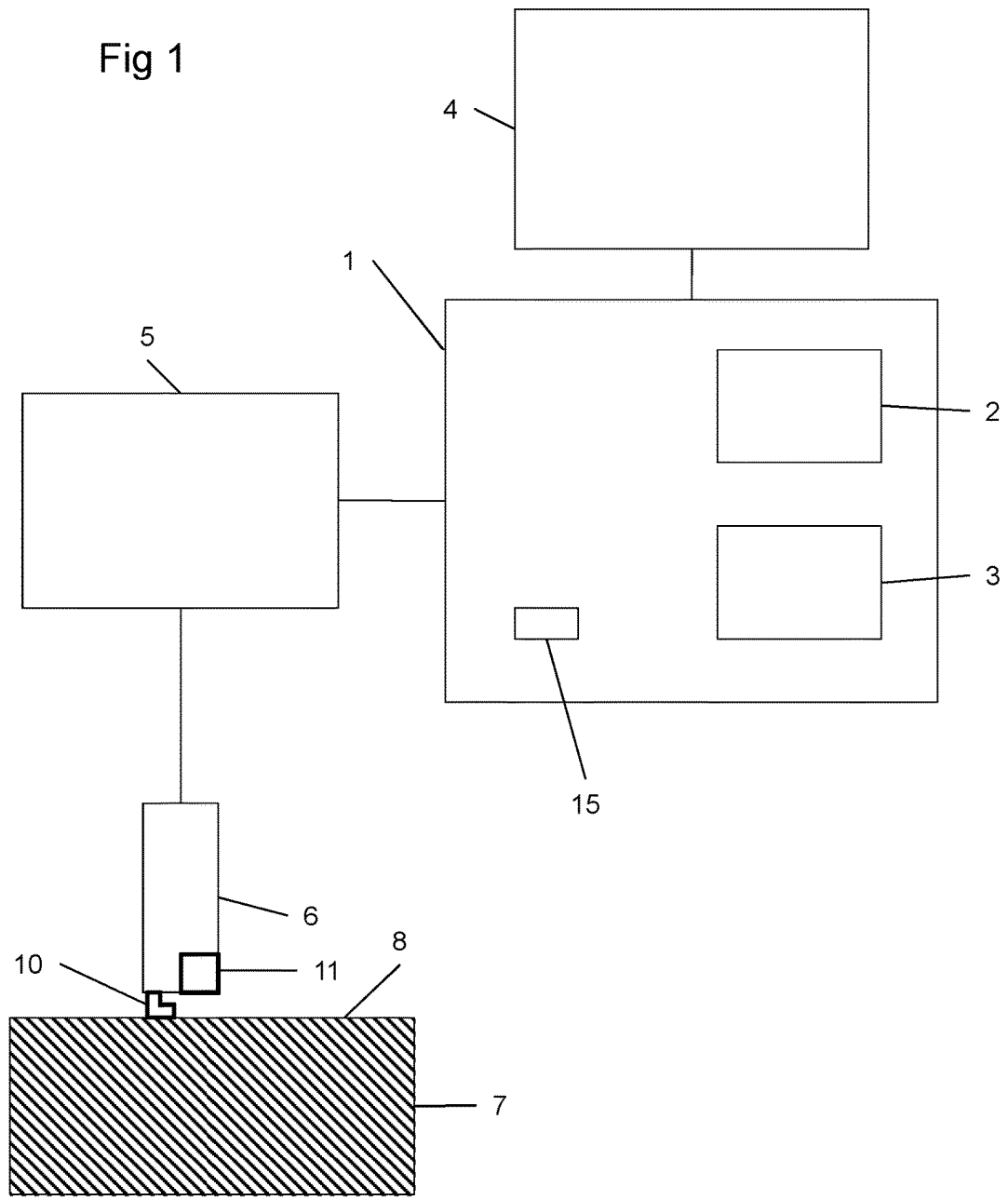
FIG. 1 shows schematically an optical coherence tomography (OCT) apparatus in accordance with an embodiment of the invention.

An optical coherence tomography (OCT) apparatus in accordance with an embodiment of the invention is shown in FIG. 1 of the accompanying drawings. This comprises a computer 1, having a processor 2 and storage 3 (such as a mass storage device or random access memory) coupled to the processor 2. The storage 3 contains data and processor instructions which cause the processor 2 to act as is described below. The computer 1 can be any suitable model; typically a personal computer running an operating system such as Microsoft® Windows® or Apple® Mac OS X® can be used. The computer 1 is also provided with a display 4 controlled by the processor 2 on which any desired graphics can be displayed, and a sound output device 15 such as a buzzer which can sound an alert noise.

The apparatus further comprises an OCT interferometer 5 and associated probe 6. The interferometer 5 interferes light reflected from sample 7 (here, a subject's skin) through probe 6 with light passed along a reference path to generate interferograms. These are detected in the interferometer 5; the measured signal is then passed to the computer 1 for processing. Example embodiments of suitable OCT apparatus can be found in the PCT patent application published as WO2006/054116 or in the VivoSight® apparatus available from Michelson Diagnostics of Orpington, Kent, United Kingdom. A stand-off 10 can be provided which spaces the probe 6 from the user's skin 7.

Such OCT apparatus typically generate multiple B-scans: that is, scans taken perpendicularly through the skin 7. The result of analysis of each interferogram is a bitmap in which the width of the image corresponds to a direction generally parallel to the skin surface and the height corresponds to the depth from the sensor into the skin. By taking multiple scans spaced apart perpendicularly to the scans—and so parallel to the skin—a stack of scans can be formed, covering a volume of the subject's skin.

The OCT apparatus takes multiple scans spaced apart in time. Successive images from the same location on a subject's skin can be used to determine the presence of blood flow through blood vessels, by determining areas that have changed between successive images. Such changes can indicate the flow of blood cells through blood vessels. Our preferred technique is speckle decorrelation OCT as described in "In vivo imaging of the microcirculation of the volar forearm using correlation mapping optical coherence tomography (cmOCT)", J Enfield, E Jonathan and M Leahy, Biomed Opt Express. May 1, 2011; 2(5): 1184-1193, but we can also use speckle variance, differencing of intensity or phase, or any other computational technique.

The time interval between the different times should be carefully selected. If the time interval is too short, then there is not enough time for blood to move through the region to make a detectable change. If the time interval is too long, then gross movements of the probe relative to the skin make it difficult or impossible to ensure that the region in the second image is exactly the same location as the region in the first image, and this results in noise in the image. In human skin, a time interval of 3.5 milliseconds works well.

An example OCT scan is shown at FIG. 2, which shows a user's skin 7, which has a surface 8. The results of comparing this to a successive image in healthy tissue are shown in FIG. 3, where areas of large differences are shown as white as indicated generally at 9. These areas represent areas where there are blood vessels. Typically, any area where change is determined at above a given threshold is determined to be a changing area.

We use these scans to determine several parameters.

Skin Atrophy

Figure 4:
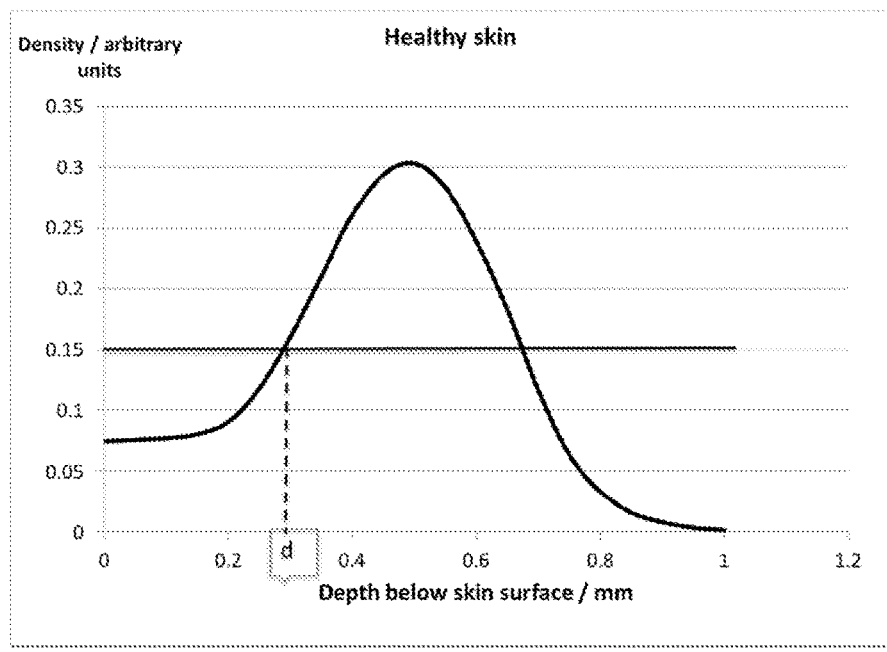
FIG. 4 shows an exemplary graph of density of varying areas with depth through healthy skin.

It is known that healthy skin comprises the epidermis, which does not contain blood vessels, and below it the dermis, which contains blood vessels of sharply increasing density with depth ("Blood Vessels and Lymphatics in Organ Systems", David I Abramson, Academic Press (28. Jan. 1984), ISBN-10: 0124121586, pp 595-32) corresponding to the transition from the 'papillary dermis' to the 'reticular dermis'. The depth distribution of time-varying regions shows an increase at this depth below the skin surface, within the dermis (as shown in FIG. 4 of the accompanying drawings for healthy skin), and then a decrease at still greater depth in the dermis due to the attenuation in the underlying OCT signal strength from optical scattering.

As such, the method described above can be used to determine the position of blood vessels in B-scan and their depth distribution. Further processing of the data is then carried out to detect adjacent time-varying regions within the stack of scans that form linear sections that may be attributed to blood vessels; and then statistical analysis of the total number, length, diameter and volume of blood vessels, as a function of depth from below the skin surface; and derivation from this data a single parameter representing the degree of atrophy of vascular structure, for example by means of a look-up table with entries in it corresponding to:

(1) the location of the skin on the body
(2) depth range at which the number density of vessels exceeds a predetermined value
(3) volume density of the vessels in the depth range; corresponding to different degrees of atrophy.

For example, a measurement may be made on the cheek of a subject, and it may be found that the number density of vessels exceeds 500 per $mm^3$ at a depth range of 200-220 microns, and the total volume of vessels in that range is 0.005 $mm^3$ per $mm^3$, and the lookup-table entry for this is 0.9, indicating a very slight atrophy compared to fully healthy skin, which by comparison will have a lookup table entry of 1.0 which may correspond to total volume of vessels in that range of 0.0075-0.0100 $mm^3$ per $mm^3$.

However, other means of arriving at a measure of vascular structure atrophy may be derived, for example an algebraic combination of one or more of vessel number density, vessel volume or average vessel aspect ratio, and the expected equivalent values from fully healthy skin, weighted according to importance for skin health.

Skin Roughness

Figure 5:
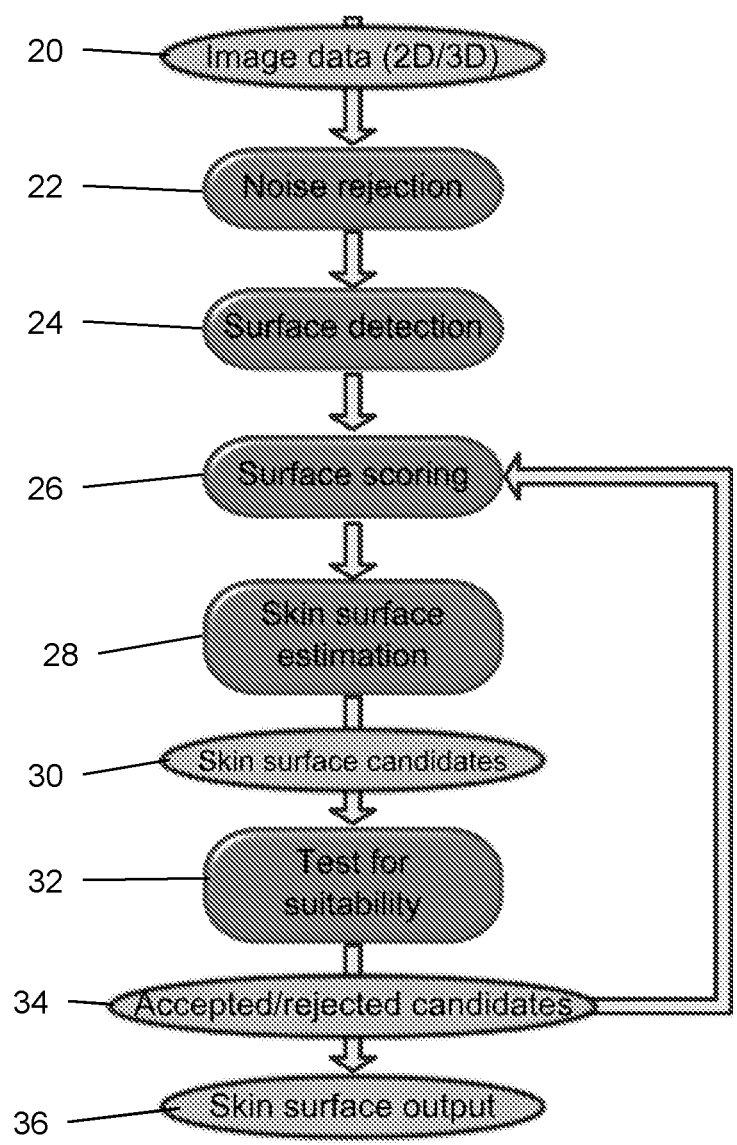
FIG. 5 shows a flowchart depicting how the apparatus of FIG. 1 determines the position of the skin surface.

The method also determines the skin roughness. In order to do so, the skin surface position must be found using the method shown in FIG. 5. In step 20, the stack of scans referred to above is generated. At step 22, in the preferred embodiment, the image data is filtered to reduce or remove random noise inherent of the coherent detection technique ('speckle noise') and other image artefacts particular to the imaging system used to capture the image data. The reduction in the effect of noise upon image contrast is achieved using linear and non-linear filtering techniques, intended to preserve edge features while removing speckle. Examples of such filters include linear filters, Kalman filters (see, for example, Igor Gurov and Maxim Volynsky "Recurrence signal processing in Fourier-domain optical coherence tomography based on linear Kalman filtering", Proc. SPIE 8792, Optical Methods for Inspection, Characterization, and Imaging of Biomaterials, 879203 (May 23, 2013); doi: 10.1117/12.2020615; http://dx.doi.org/10.1117/12.2020615) or wavelet filters (see, for example, "Speckle reduction in optical coherence tomography images of human finger skin by wavelet modified BM3D filter", Bo Chong, Yong-Kai Zhu, Optics Communications Volume 291, 15 Mar. 2013, Pages 461-469, http://dx.doi.org/10.1016/j.optcom.2012.10.053).

The unadulterated proximal tissue surface represents a refractive index change from that of air to that of tissue and therefore presents a very strongly backscattering feature and high signal in OCT images. At step 24, to obtain candidates for skin surfaces in images, therefore, the image A-lines are filtered to indicate extrema in the OCT signal; certain of these are rejected based on simple parameters (position, classification and the local environment of the extrema, such as the difference between the positions of the extrema in adjacent images). Further edge-filtering may be employed to refine results and ensure that the estimations of skin surface are minimally affected by remaining speckle or a poorly-backscattering skin surface (in the presence of, for example, media which reduces or minimises the difference in refractive index at the proximal side of the skin surface).

The result of this stage is a 3D binary array of possible surface positions, with multiple solutions possible in each A-scan of the data array.

The process in step 24 may typically result in multiple candidates for the proximal skin surface. Step 26 is undertaken therefore to assign a score to each candidate in each A-scan according the probability that it does not represent the true skin surface. This algorithm may involve multiple independent estimates of probability and combine these in a suitable manner to provide a meaningful metric.

In step 28, the set of multiple skin surface candidates and their weights are then processed to select a set of candidates 30 representing a single surface. The algorithm employed to select this surface attempts to minimise the sums of the weights of candidates in the selected surface and also a weight assigned to the Euclidean distance between neighbouring candidates in the selected surface.

In step 32, the surface 30 selected in step 28 is assessed for suitability according to criteria based on a-priori knowledge of skin morphology, the result of this assessment is termed herein "the worthiness" of the surface. The criteria may include uniformity, periodicity of variation, surface variance amongst other factors, all being within expected limits from known skin samples. If an insufficient worthiness is attained, according to a prescribed value, the solution is rejected (at step 34) and steps 26, 28 and 32 repeated using an additional weighting factor derived in this step. The additional weighting assigned to the multitude of candidates in the repeated step 28 may be calculated based on the position of the surface and its overall worthiness as well as localised contribution to the worthiness of particular candidates.

As part of the determination of the skin surface position, it is also convenient to determine the roughness of the skin surface. Three parameters, the mean deviation of the skin position ($R_a$), the range of the skin position from highest peak to lowest valley ($R_z$) or the root mean square deviation of the skin position ($R_q$) can be measured. In order to eliminate the effect of large-scale surface undulations (such as, for example, skin surface inclination relative to the imaging probe, caused by inaccurate probe positioning) without making undue requirements of the user, skin surface topography is measured by calculating the deviation of the detected skin surface from the corresponding point in a calculated mean skin surface. This mean skin surface is calculated using a spatial low-pass filter and mathematically fitting a smooth-curved surface to the resultant profile; see, for example Kottner, J., Schario, M., Bartels, N. G., Pantchechnikova, E., Hillmann, K. and Blume-Peytavi, U. (2013), Comparison of two in vivo measurements for skin surface topography. Skin Research and Technology, 19: 84-90. doi: 10.1111/srt.12009, or B-G Roséen et al (2005) On in-vivo skin topography metrology and replication technique, J. Phys.: Conf. Ser. 13 325 doi: 10.1088/1742-6596/13/1/076.

Skin Structure

Skin consists of a number of layers, the principle of these are the epidermis and dermis; however these are further subdivided into sub layers, for example the papillary and reticular dermis, and the strata spinosum, granulosum and basale. Healthy skin is characterised by well differentiated layers that can be clearly distinguished by a trained observer looking at an OCT image, and also by the appearance of texture within the layers that corresponds to healthy growth of vessels, collagen and other material in an ordered manner. Unhealthy skin is characterised by loss of clarity of the layer structure, loss of ordered texture, increased attenuation of OCT signal with depth, and the appearance of clumps, swirls and other irregularities that are very localised and can be identified in OCT images by a trained observer.

These characteristics may be analysed from the OCT images by numerical methods, for example by dividing the OCT data in a scanned region into small sub-volumes at predetermined depths below the skin surface; calculating the average OCT intensity in each sub-volume; and calculating the mean and standard deviation of these in each depth layer; and then comparing the results for each depth layer with the expected results for healthy skin in a look-up table. However, other numerical methods may equally well be employed.

Skin Reflectivity

Having obtained the skin topography, it is possible to measure the skin reflectivity. This may be done simply by finding the average intensity of all of the OCT signal of pixels that are found at the top surface of the skin (determined in the roughness measurement above) within the scanned region. A more refined measurement may be obtained by calculating a weighted average of the intensity of pixels within a predetermined depth of the top surface of the skin, with greater weight being assigned to the top surface and linearly less weight to pixels with greater depth.

Skin Tone

The probe 6 is also provided with a colour camera 11 arranged to view the skin surface 8. This can be provided with a light source with a known spectrum, such as a white light emitting diode (LED, not shown). Typically, the camera will provide three colour channels, namely red, green and blue; by determining the mean value of each of these, it is possible to determine the skin tone of the subject, typically on a scale such as the Fitzpatrick scale of pale white, white, cream white, moderate brown, dark brown, dark brown/black. Because a mean measurement is being used, there is no need as far as this method is concerned for accurate focussing of the camera 11 on the skin surface, as an unfocussed image will suffice.

Producing a Combined Measurement

The parameters above are then combined to form a combined measurement. The combined measurement may, for example, provide a measure of skin health that may correspond to the skin of an 'ideal subject' in terms of years of additional ageing. For example, a 30 year old male subject who has very healthy skin which has parameters measured to be close to the 'ideal male subject' with the same age, 30 years, as the subject, has a skin age factor of 0 years; whereas a 30 year old male whose skin measurements correspond to that of a 40-year old 'ideal male subject' would have a skin age factor of +10 years. To arrive at the skin age factor, the gender, subject age, scan location, skin roughness, vascular atrophy and skin tone parameters would be used as indexes into a look-up table containing the corresponding age factors. Typically, there would be a look-up table per skin tone.

The 'skin structure disorder' parameter may be used to further refine the derivation of the 'skin age factor' described above, for example by modifying the vascular atrophy 'score' up or down.

The final score is of use to a dermatologist looking to determine the effects of aging on the subjects, and to other professionals, including salespeople selling cosmetic products who can use this information to target their sales to the most relevant consumers. Depending on the user, the present system could also output the individual parameters (roughness, vascular atrophy, and structural disorder and reflectivity) because these parameters can also be useful to the dermatologist or other professional individually and in combination.

The invention claimed is:

1. A method of processing optical coherence tomography (OCT) scans through a subject's skin, the method comprising:
    receiving at least one OCT scan through the subject's skin, each scan representing an OCT signal in a slice through the subject's skin;
    processing each OCT scan so as to determine a set of parameters comprising at least a measure of the atrophy of the vascular structure in the epidermis;
    in which the processing produces a measurement of skin condition dependent upon each of the set of parameters, and the method comprises outputting the measurement of skin condition; wherein the determination of the measure of skin atrophy comprises determining the position of blood vessels in the user's skin, determining a distribution of a numerical density of blood vessels with depth through the user's skin, and determining a threshold depth in the distribution moving through the user's skin from the skin's surface through the skin at which the numerical density of blood vessels in the user's skin exceeds or reaches a threshold.

2. The method of claim 1, in which the determination of the measure of atrophy, and/or the measure of atrophy itself, comprise a determination of the volume density of blood vessels at the threshold depth.

3. The method of claim 2, in which the measure of atrophy is determined based upon the volume density, using a lookup table which maps the volume density together with at least one of the location of the user's skin on the user's body, the threshold depth, the age and gender of the user to a value forming the measure of atrophy.

4. The method of claim 1, in which the set of parameters comprises the skin structure as a function of the depth through the skin.

5. The method of claim 4, in which the determination of the skin structure comprises the identification of layers within the user's skin, and the comparison of the intensity of the scans within each layer to an expected intensity for each layer.

6. The method of claim 5, comprising determining the mean and/or standard deviation intensity within at least one sample area in each layer, and comparing the mean and/or standard deviation intensity within each layer to an expected mean and/or standard deviation intensity for each layer.

7. The method of claim 4, in which the method comprises determining the mean attenuation coefficient within each layer.

8. The method of claim 1, further comprising determining a set of additional parameters otherwise than from the OCT scans, and using each of the set of additional parameters in the determination of the measurement of skin condition.

9. The method of claim 8, in which the set of additional parameters comprises the skin tone of the subject.

10. The method of claim 9, in which the determination of the skin tone of the subject comprises imaging of the region of skin scanned with OCT with a camera attached to the OCT probe to form a captured image.

11. The method of claim 10, in which the camera is equipped with a light source, which has a known spectrum in the visible wavebands.

12. The method of claim 10, in which the determination of the skin tone of the subject comprises analysing the resulting colour of the captured image of the skin.

13. The method of claim 1, in which the determination of the measurement of skin condition comprises the comparison of each of the parameters with a predetermined value for that parameter and assigning measurement of skin condition based upon a divergence between the parameter and the predetermined value.

14. The method of claim 13, in which the predetermined value is age and/or gender and/or skin type dependent.

15. An optical coherence tomography (OCT) image processing apparatus, comprising a processor, a display coupled to the processor and storage coupled to the processor, the storage carrying program instructions which, when executed on the processor, cause it to carry out the method of claim 1.

16. The apparatus of claim 15, comprising an OCT apparatus by means of which the OCT scans are captured.

17. The apparatus of claim 16, comprising an OCT probe arranged to generated interferograms, and the processor may be arranged to generate the images from the interferograms, typically as they are captured.

18. The apparatus of claim 15, being separate from any OCT apparatus typically being arranged to process the images subsequent to their capture.

19. The apparatus of claim 15, comprising a camera arranged, in use, to view an area of the surface of the subject's skin in the region of the OCT scans.

20. A method of processing optical coherence tomography (OCT) scans through a subject's skin, the method comprising:
    receiving at least one OCT scan through the subject's skin, each scan representing an OCT signal in a slice through the subject's skin;
    processing each OCT scan so as to determine a set of parameters comprising at least a measure of the atrophy of the vascular structure in the epidermis;

in which the processing produces a measurement of skin condition dependent upon each of the set of parameters, and the method comprises outputting the measurement of skin condition; wherein the set of parameters comprises the skin reflectivity; and wherein the determination of the skin reflectivity comprises calculating a weighted average of the intensity of pixels in the OCT scan within a predetermined depth of the top surface of the skin, with greater weight being assigned to the top surface and less weight to pixels with greater depth.

21. The method of claim 20, in which the determination of the skin reflectivity comprises finding the average intensity of the OCT signal in each scan at the top surface of the user's skin.

22. An optical coherence tomography (OCT) image processing apparatus, comprising a processor, a display coupled to the processor and storage coupled to the processor, the storage carrying program instructions which, when executed on the processor, cause it to carry out the method of claim 20.

23. The apparatus of claim 22, comprising an OCT apparatus by means of which the OCT scans are captured.

24. The apparatus of claim 23 comprising an OCT probe arranged to generated interferograms, and the processor may be arranged to generate the images from the interferograms, typically as they are captured.

25. A method of processing optical coherence tomography (OCT) scans through a subject's skin, the method comprising:
- receiving at least one OCT scan through the subject's skin, each scan representing an OCT signal in a slice through the subject's skin;
- processing each OCT scan so as to determine a set of parameters comprising at least a measure of the atrophy of the vascular structure in the epidermis;
- in which the processing produces a measurement of skin condition dependent upon each of the set of parameters, and the method comprises outputting the measurement of skin condition; wherein the set of parameters comprises the skin roughness; in which the determination of the skin roughness comprises the determination of at least one of the mean deviation of the skin position from the mean skin position, the range of skin position from the highest peak to lowest valley and the root mean square deviation of the skin position.

26. An optical coherence tomography (OCT) image processing apparatus, comprising a processor, a display coupled to the processor and storage coupled to the processor, the storage carrying program instructions which, when executed on the processor, cause it to carry out the method of claim 25.

27. The apparatus of claim 26, comprising an OCT apparatus by means of which the OCT scans are captured.

28. The apparatus of claim 27, comprising an OCT probe arranged to generated interferograms, and the processor may be arranged to generate the images from the interferograms, typically as they are captured.

29. A method of processing optical coherence tomography (OCT) scans through a subject's skin, the method comprising:
- receiving at least one OCT scan through the subject's skin, each scan representing an OCT signal in a slice through the subject's skin;
- processing each OCT scan so as to determine a set of parameters comprising at least a measure of the atrophy of the vascular structure in the epidermis;
- in which the processing produces a measurement of skin condition dependent upon each of the set of parameters, and the method comprises outputting the measurement of skin condition; wherein the measurement of skin condition comprises an age difference between a predetermined skin condition for a user of given age and/or gender and/or skin type and the condition of the skin as determined based on each parameter; and wherein the determination of the measurement of skin condition comprises the determination of a partial age difference based on each parameter, and then combining each of the partial age differences.

30. The method of claim 29, in which each the partial age difference is determined by using a lookup table for each parameter, each lookup table mapping the parameter to a partial age difference.

* * * * *